United States Patent [19]
Heseltine et al.

[11] Patent Number: 5,983,211
[45] Date of Patent: Nov. 9, 1999

[54] METHOD AND APPARATUS FOR THE DIAGNOSIS OF COLORECTAL CANCER

[76] Inventors: Gary L. Heseltine, Star Rte. Box 86, Mico, Tex. 78056; Richard E. Warrington, 18706 Capetown Dr., Houston, Tex. 77058

[21] Appl. No.: 09/127,008

[22] Filed: Jul. 31, 1998

Related U.S. Application Data

[63] Continuation of application No. 08/788,661, Jan. 24, 1996, Pat. No. 5,790,761.

[51] Int. Cl.[6] .............................. G06E 1/00; G06E 3/00; G06F 15/18
[52] U.S. Cl. .................................. 706/15; 706/38; 706/48
[58] Field of Search .................................. 706/15, 38, 48

[56] References Cited

U.S. PATENT DOCUMENTS 5,790,761  8/1998  Heseltine et al. ......................... 706/16

*Primary Examiner*—Tariq R. Hafiz
*Assistant Examiner*—W. Starks
*Attorney, Agent, or Firm*—Gunn & Associates

[57] ABSTRACT

A process is set forth in which cancer of the colon is assessed in a patient. The probabilities of developing cancer involves the initial step of extracting a set of sample body fluids from the patient. Fluids can be evaluated to determine certain marker constituents in the body fluids. Fluids which are extracted have some relationship to me development of cancer, precancer or tendency toward cancerous conditions. The body fluid markers are measured and other quantified. The marker data then is evaluated using a nonlinear technique exemplified through the use of a multiple input and multiple output neural network having a variable learning rate and training rate. The neural network is provided with data from other patients for the same or similar markers. Data from other patients who did and did not have cancer is used in the learning of the neural network which thereby processes the data and provides a determination that the patient has a cancerous condition, precancer cells or a tendency towards cancer.

20 Claims, 1 Drawing Sheet

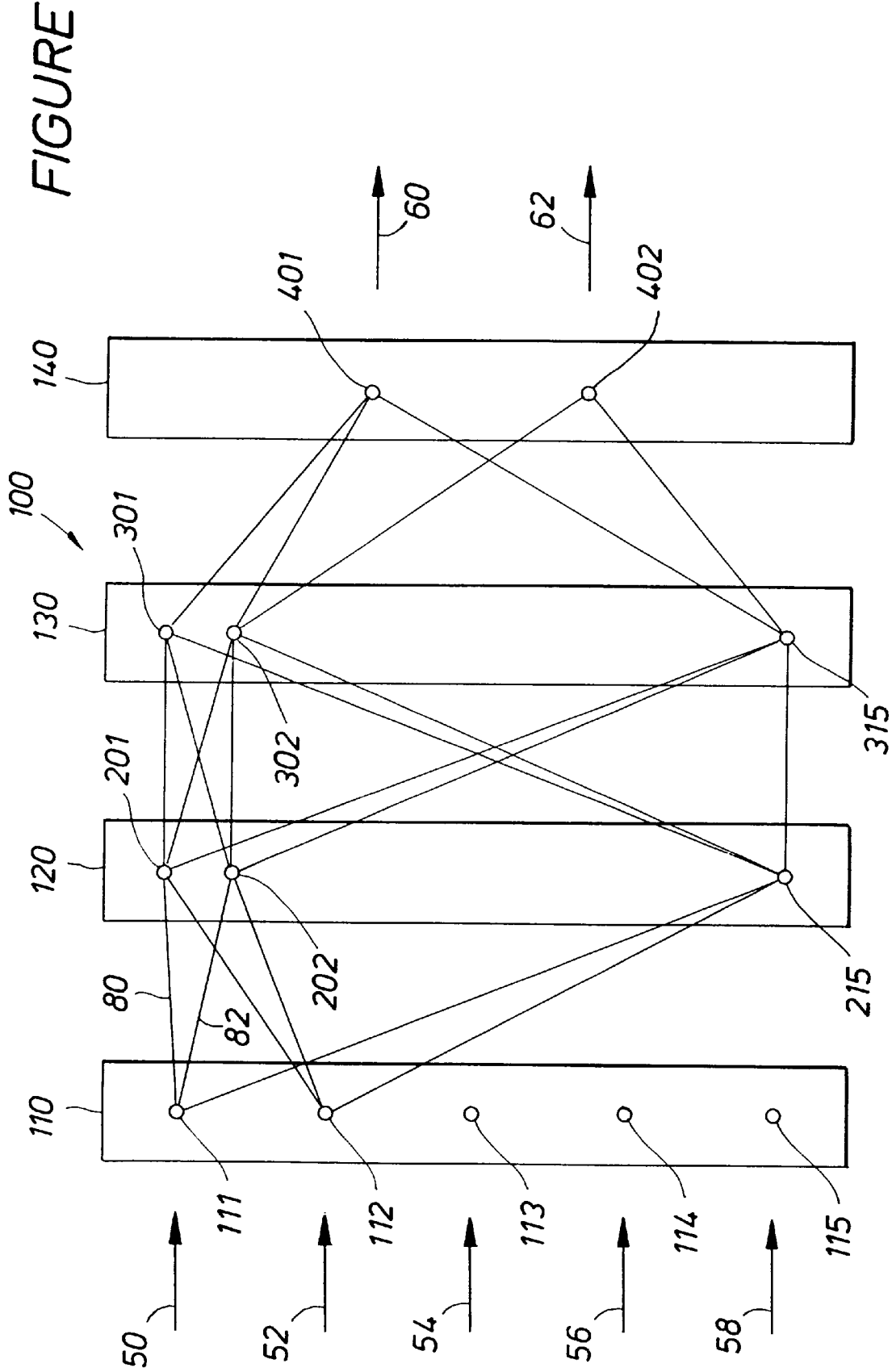

METHOD AND APPARATUS FOR THE DIAGNOSIS OF COLORECTAL CANCER

This is a Continuation Application of application Ser. No. 08/788,661 filed on Jan. 24, 1996, now U.S. Pat. No. 5,790,761.

FIELD OF THE DISCLOSURE

The present invention relates to a method and system for computer aided differential diagnosis of colorectal cancer, and in particular, computer aided differential diagnosis using neural networks.

BACKGROUND OF THE INVENTION

Computer aided differential diagnosis of diseases has become important to such fields as cardiology, radiology, and areas of medicine using ultrasonography. These have the benefit of images or time dependent signals. In these fields, differential diagnosis of disease permits the health care provider to more accurately distinguish between many diseases that can produce similar radiographs, electrocardiograms or sonographs (i.e., signals or images). Differential diagnosis, in one embodiment of this invention using neural networks, is applied in the detection ol colon cancer. The present invention pertains to diagnosis of colorectal cancer by analyzing a combination of biological indicators, markers, obtained from body tissues or fluids (including biological waste excretions). The set of markers used are chosen from cancer markers determined to be associated with colorectal cancer. The patient's biological samples are assayed across a set of markers. This analysis yields a set of input data which is processed using a non-linear logic analysis technique known as a neural network. This technique permits healthcare professionals to assess (1) whether the patient is at risk of developing colorectal cancer; (2) whether the patient has colorectal cancer; (3) the state of the patient's disease; (4) what medical treatment would be effective on that patient's disease; and/or (5) the efficacy of a particular treatment modality on the individual patient's disease (surgery, chemotherapy, radiation or a combination of modalities).

For most forms of cancer, if the site is not readily ascertainable to the physician, disease detection frequently occurs when the disease has progressed beyond a state where medical intervention is most beneficial to the patient. For colorectal cancer, currently available means of cancer detection are highly invasive and/or particularly expensive. These methods include exploratory surgery, sigmoidoscopy, colonoscopy, biopsy and internal imaging techniques such as CAT scans and MRI (magnetic resonance imaging).

The scientific discovery that cancer cells exhibit certain proteins, ribonucleic-(RNA) and deoxynucleic acids (DNA), commonly known as biological markers, led to a surge of hope in the biomedical community that a less non-invasive means of detecting cancer would soon be available. Unfortunately, the majority of cancer markers are shared among widely disparate forms of cancer. Furthermore, analysis of markers from biological fluids, for example urine and blood, have resulted in low accuracy with respect to cancer detection.

This invention is a method and apparatus for sensing and classifying a condition of interest in the presence of poor or unknown statistical relationships, in this instance, colorectal cancer. The parameter representative of the condition of interest, a biological marker found to be statistically associated with colorectal cancer, is sensed and an electrical signal or measure representative of the sense parameter is produced. The electrical signal is converted into a digital signal; this digital signal contains a measure representative of the condition of interest and having an unknown or fuzzy relationship. The digital signal is input to an artificial neural network which enhances the relationship to cancer occurrence. It is this unclear or ambiguous correlation that has prevented biological markers for purposes of cancer detection from being efficacious. The digital signals of selected markers are input to an artificial neural network which filters out the "background noise" to produce a filtered output signal from the digital signals, and classifies the output signal of interest from the filtered signal to produce an output representative of the determined signal. In the embodiment described herein, the differential diagnosis of cancer for purposes of diagnosis, prognosis and risk evaluation of developing cancer can all be derived through processing marker data in the neural network system.

An artificial neural network conceptually has several neuron elements (units) and connections between them. These units are categorized into three different layers or groups according to their functions. A first layer defined as an input layer receives the data entered into the system. A second layer defined as the output layer delivers the output data representing an output pattern. A third set of units comprises a number of intermediate layers, also known as hidden layers, that convert the input pattern into an output. This novel method of diagnosing colorectal cancer inputs clinical parameters (such as age, sex, weight, etc.) and marker data into the neural network.

Colon cancer is one of the leading causes of cancer death in the United States, with approximately 60,000 attributable deaths annually. Silverberg et al., 39 CANCER 3 (1989). Scientific evidence suggests that the majority of colon cancers arise from the evolution of normal muscosa progressing into adenomas and finally to adenocarcinomas. Morson, 5 Clin. GASTROENTEROLOGY 505 (1976). Adenoma removal correlates with a reduced risk of rectal carcinomas; analogously, the removal of adenomatous polyps, reduces the likelihood of colon cancer, see Winawer et al., 100 GASTROENTEROLOGY A410 (1991).

Disease diagnosis based on biochemical analysis of a patient's tissue and biological fluid samples is basic to modern medicine. Occasionally, the presence of a single biological substance or marker within a biological sample is sufficient for the determination of a particular disease. Unfortunately single marker cancer detection has proven unreliable, especially when attempting to detect cancer at is early stages. Oftentimes, when cancer detection is indicated by the presence of a single marker, the disease has reached an advanced state and the patient has a correspondingly poor prognosis. As a result, a test has long been sought that is both non-invasive as well as efficacious in the diagnosis of colon cancer.

Historically, colorectal cancer risk prediction has been hindered due to the cancer site and the difficulty in accurately assessing the surrounding tissue for cell abnormalities. Furthermore, cancer risk prediction requires correlating the relationship not only of biological factors such as markers, but also additional diverse clinical factors such as race, sex, family history, environmental actors, and prior colorectal polyp development (if any). The invention can correlate all this data and is beneficial in several ways. First, non-invasive procedures such as phlebotomy decrease the cost to the patient for testing and as a direct result becomes more widely accessible to the general population at a reduced cost. The invention herein also increases the accuracy and efficacy over existing testing procedures by assessing data with relationship to other factors.

Currently, most techniques for screening patients for developing or developed cancer are highly invasive and/or particularly expensive, for example exploratory surgery, biopsy, and internal imaging techniques such as CAT scan and NMR imaging. The present invention is less invasive than surgery or biopsy and relatively inexpensive by comparison, requiring only the taking of fluid samples such as a blood sample, analyzing that sample for particular markers using known techniques, and then processing the marker analysis data using the method of the present invention.

Many of the proteins and protein fragments (including their corresponding genes) present within the body have been shown to act as helpful indicating markers in the diagnosis of disease. A single protein marker does not represent a disease state precisely, however. Several proteins or their gene equivalents more accurately define the disease state, as cancer onset and progression occurs over multiple stages or steps. There will be some association to the individual proteins which act as good markers for a particular disease; there is no totally unique marker to a disease while several of the good markers (in combination) indicate the presence of the disease or a high risk that the disease will soon develop. Another problem with the use of a single marker to test the disease presence is that certain markers are common to more than one disease, introducing the probability of an incorrect diagnosis. Therefore, using a combination of markers increases the accuracy of disease diagnosis and reduces ambiguity.

Proteins and/or their corresponding genes are present in the body at all times. The concentration of gene products, such as proteins or ribonucleic acid (RNA) can determine whether a patient is healthy or diseased. Protein concentrations generally do not conform to a statistically normal distribution (or linear mathematical functions) between individuals. Since real world phenomena are often non-linear, the application of non-linear logic techniques to a predetermined combination of protein marker concentrations provides the best hope to determine the correlation between the various markers and marker combinations and the diagnosis of the disease in question.

U.S. Pat. No. 4,338,811 to Miyagi, et al., issued Jul. 13, 1982 describes a method and apparatus for diagnosis of disease. A two-dimensional pattern diagram representing the relation between integrated values of peaks and the retention times in a chromatogram of substances in a body fluid of a subject person is spatially compared with a two-dimensional pattern representing the same relationships for both normal and diseased persons. Siguel et al., in U.S. Pat. No. 5,075,101, issued Dec. 24, 1991, discloses a method for diagnosis of fatty acid or lipid abnormalities. It discloses a disease diagnostic method for lipid and fatty acid biochemical status; and analytically comparing patterns or domains obtained from indices of the subject with similar indices derived from tissues of subjects with normal and abnormal biochemistry.

Moses E. Cohen et al., in "Use of Pattern-Recognition Techniques to Analyze Chromatographic Data", *Journal of Chromatography*, Vol. 384, pp. 145–152 (1987) describes the use of decision making algorithms, often denoted expert systems, for the analysis of chromatographic data. In particular, a pattern recognition technique was established using a new class of orthogonal polynomials developed by Cohen. The technique is based on a supervised learning approach, and allows classification of data into two or more categories. In the paper, the usefulness of the technique in the analysis of chromatographic data is illustrated by its application to the diagnosis of bacterial infection of patients with liver disorders by the use of chromatograms obtained from ascetic fluid taken from the patients. Subsequently, in "Medical Diagnosis and Treatment Plans Derived from a Hybrid Expert System," *Hybrid Architectures for Intelligent Systems*, Abraham Kandel and Gideon Langholz, eds. CRC Press, Boca Raton, Fla., 1992, pp. 330–344, D. L. Hudson, et al. describe the use of neural network approaches in diagnosing metastatic melanoma from chromatographic analysis samples of urine.

Further work by Cohen et al. pertaining to use of Neural networks in the diagnosis of disease is described in "Neural Network Approach to Detection of Metastatic Melonoma from Chromatographic Analysis of Urine", from the *Proceedings Annual Symp. Computer Appl. Med. Care*, pp. 295–299 (1991). In these proceedings, Cohen et al. discuss in detail the melanogens present in the urine of patients with metastatic melanoma, the constituents of which were used to develop clinical correlations, and the neural networks model used to develop a prospective decision aid which can be used by the clinician as a good indicator of the current state of metastatic disease in each patient.

Dr. William G. Baxt describes the "Use of an Artificial Neural Network for the Diagnosis of Myocardial Infarction" in the *Annals of Internal Medicine*, Vol. 115, pp. 843–848 (1991). An artificial neural network was trained to diagnose, with a high degree of accuracy, acute myocardial infarction in patients presenting to an emergency department. The neural network structure included a "back propagation" algorithm of the kind commonly used in neural network software, to determine the "weights" applied to the input data types and hidden layer variables within the network. This algorithm is used to minimize error in network output, i.e., to minimize the difference between the network output for a specific training pattern and the expected output of that training pattern. The data input to the neural network were selected from the patient presenting symptoms, the past history findings, and the physical and laboratory findings of patients presented with anterior chest pain.

Peter M. Ravdin et al., in "A demonstration that breast cancer recurrence can be predicted by neural network analysis", *Breast Cancer Research and Treatment*, Vol. 21, pp. 47–53 (1992), describe the use of neural network analysis to successfully predict the clinical outcome of node-positive breast cancer patients. During training, the network received as input information tumor hormone receptor status, DNA index and S-phase determination by flow cytometry, tumor size, number of axillary lymph nodes involved with tumor, and age of the patient, as well as length of clinical followup, relapse status, and time of relapse.

John N. Weinstein et al. describe "Neural Computing in Cancer Drug Development: Predicting Mechanism of Action", in *Science*, Vol. 258, pp. 447–451 (Dec. 16, 1992). Neural networks are described as being capable of predicting a drug's mechanism of action from its pattern of activity against a panel of 60 malignant cell lines in the National Cancer Institute's drug screening program.

In accordance with the present invention, a connectionist, non-linear logic analytical technique has been used in combination with specific biological indicators (markers) obtained from body tissue or fluids to determine whether a patient has a colorectal cancer or is at risk sufficiently toward developing colorectal cancer that the probability of formation of a cancer is likely. A neural network diagnosing colorectal cancer using biological indicator input was developed, the network comprises:

a) an input layer having a set of marker inputs;
b) at least one hidden layer, wherein each hidden layer has at least five processing elements; and
c) an output layer having at least one output.

The preferred neural network comprises an input layer having about four to ten marker inputs; a number of hidden layers ranging from about 2 to about 15, wherein the total number of processing elements included in the hidden layers ranges from about 24 to about 100; and an output layer having at least 2 outputs.

A neural network of the kind described in combination with markers selected from biological indicators known to have a significantly better relationship with colorectal cancer to serve as a significant indicator of the development of or presence of such cancer. The biological indicators, referred to as markers, are in and selected from the group of markers and include: Carcinoembryonic Antigen (CEA); Alpha-Fetoprotein Modified or Increased Analytical Precision (AFP); Pancreatic Oncofetal Antigen (POA); Antigen Specific for #1116-N5'-19-9 Antibody; Lipid-Bound Sialic Acid (LSA); New oncogenes; Myc oncogenes; Ras oncogenes; Centocor CA 72/4 (a measurement of tumor-associated Glycoprotein 72 (TAG-72) using epitope-specific antibody # B72-3); Antibodies for the p53 gene; Antibodies to Laminin $-P_1$; Yale Col. Sr. Factor; Harvard Uninary Gonadotropin Peptide (UGP); Tumor Suppressor Gene p53; and antibodies to the markers listed in cases where the marker is not an antibody. The DNA and DNA fragment precursors of a protein in addition to the protein can be used as markers. Glycoproteins, lipoproteins and flycolipids frequently are biological indicators of abnormal cell growth.

BRIEF DESCRIPTION OF THE DRAWING

A single FIGURE illustrates an example of a neural network used in the invention, comprising an input layer comprising five processing elements, two hidden layers each comprising fifteen processing elements, an output layer comprising two processing elements, and sample interconnections between the processing elements.

DETAILED DESCRIPTION OF THE PREFERRED EMBODIMENTS

Biological indicators or markers, as used in the specification and claims herein is intended to include carbohydrates, lipids and proteins as well as combinations thereof; also, amino acids, peptides, and nucleic acids.

Connectionist network, as used in the specification and claims herein is intended to mean a network of processing elements or neurons which are highly interconnected to each other.

Encoding scheme, as used in the specification and claims herein is intended to mean a method of representing data or information.

Interconnected, as used in the specification and claims herein is intended to mean to connect to or be connected with one or more processing elements by weighting factors (weights).

Learning rate, as used in the specification and claims herein is intended to mean a contrast factor which affects the rate at which the weighting factors (weights) between processing elements change.

Processing element, as used in the specification and claims herein is intended to mean an element which calculates its own output by finding the weighted sum of the inputs, generating an activation level and passing the value to an output or transfer function.

Processing layer, as used in the specification and claims herein is intended to mean a layer of processing elements.

Training tolerance, as used in the specification and claims herein is intended to mean the tolerance or amount of variation permitted between a network generated value and the target value.

Transfer function, as used in the specification and claims herein is intended to mean a function used to generate an output from a processing element.

The present invention pertains to a non-linear, connectionist analytical system with biological indicators taken from body tissues or fluids to diagnose whether a patient has colorectal cancer or a high probability of developing colorectal cancer.

Disease markers are broadly defined as those biochemical substances produced by tumors or by the host in response to the presence of disease. When disease markers are present in tissues or the circulation system in abnormal amounts, they can indicate the presence of malignant disease. Several comprehensive reviews have summarized the variety of biochemical substances or indicators that have been shown to have proven use or potential application as tumor markers. However, none of these substances have yet been demonstrated to be specific products of neoplasia. In general, the low clinical sensitivity and clinical specificity of tumor marker tests for cancer preclude their use for cancer screening in the general population.

Another aspect of the use of markers for early cancer detection is the easy specimen collection for data evaluation. Most studies performed to date have used single point determinations of the markers, comparing the test values to the established cut off values or an upper limit of "normal", as defined by statistical methods. Cut off values are usually set high to avoid reporting a non-malignant condition as a malignancy, and thus are not useful for identifying early abnormalities in the tumor marker values. The present invention identifies particular tumor markers which are sufficiently related to colorectal cancer to be useful in predicting the presence or developing presence of the disease, and combines these markers in a non-linear, connectionist analytical system which permits the analysis of individual patient data to diagnose the presence or developing presence of colorectal cancer.

Non-linear, connectionist analytical systems such as neural networks are a relatively recent development in the information sciences, an outgrowth of artificial intelligence research in the 1950's and 1960's. Algorithms for use in neural networks have progressed to the extent that they are useful in analyzing input data as complexly interrelated as necessary to implement the present invention. Neural networks are so named because they exhibit certain analogies, at least superficially, to the way in which arrays of neurons most likely function in biological learning and memory. They differ from the usual computer programs in that they "learn" from a set of examples. They are not programmed to get the right answer. Data weighting is done primarily in the network. The architecture of a neural network used in a preferred embodiment of the present invention is defined by network definition. This neural network analyzes biological indicators related to colorectal cancer, providing a method of diagnosing the presence of colorectal cancer or a high probability of its development. The neural network architecture is merely illustrative and not intended to limit the potential neural network as used in the present invention.

A representative neural network comprises 4 to 10 input processing elements in the input processing layer, 15 processing elements in the first hidden processing layer, 15 processing elements in the second hidden processing layer, and 2 to 4 output processing elements in the output processing layer.

The preferred neural network used in the present invention includes a back propagation algorithm. Specifically, the software is Brainmaker Professional V 2.51, available from California Scientific Software of Nevada City, Calif. However, there are numerous other neural network software packages which can be used in the present invention, for example "NETS," available from the University of Georgia Computer Software Management and Information Center, Athens, Ga.; "Mathematica," available from Wolfram Research, Inc., Champaign, Ill.; and "NeuDesk 2," available from Neural Computer Sciences, Totton, Southampton, Hampshire, SO4, 3WW.

Each input processing element in the input layer receives a biological indicator ("marker") measured by independent testing and analysis and may be related to the realized presence or developing presence of colorectal cancer. The marker samples are obtained from tissue or fluid specimens taken from patients for diagnosis. Each sample is processed using a biochemical technique. The units of the processing result are dependent on the biochemical testing technique used. It does not matter that the units of different marker data are or are not the same, so long as the units are consistent for a given marker during the training of the neural network; restated, for a trained neural network, the marker units input to the trained network must be the same units used when the network was trained.

The input markers used to train the neural network are data from an individual at a single sample taking laboratory visit, or they can be collected over time, wherein a number of markers are gathered from a single patient over a few days.

The input marker values used to train neural network in the present instance are obtained from a single diagnostic session for each patient. Due to the ability of the neural network to process non-linear data in a manner which develops the interrelationships between the markers input, relatively good performance is obtained by the method of the invention.

It is preferable to have periodic data for a large number of patients, as this should provide enhanced sensitivity and specificity in the diagnostic result obtained. In particular, sequential or periodic data provides improved diagnostic performance relative to the development of disease states.

The following is a list of markers sufficiently related to the presence or developing presence of colorectal cancer that they are useful in the diagnosis of this disease. Additional markers can be added to this listing for use in the present invention. The markers presently known include Carcinoembryonic Antigen (CEA); Alpha-Fetoprotein Modified for Increased Analytical Precision (AFP); Pancreatic Oncofetal Antigen (POA); Lipid-Bound Sialic Acid (LSA); Antigen Specific for #1116-N5'-19-9 Antibody; New oncogenes; Myc oncogenes; Ras oncogenes; Centocor CA 72/4 (a measurement of tumor-associated Glycoprotein 72 using epitope-specific antibody #B 72-3); Antibodies for the p53 gene; Antibodies to Laminin $-P_1$; Yale Col. Sr. Factor; Harvard Urinary gonadotropin Peptide (UGP); Tumor Suppressor Gene p53; and antibodies to said markers in cases wherein said marker is not an antibody. It is understood that DNA and DNA fragment precursors of a protein and that protein can be used alternatively as markers. Related glycoproteins, lipoproteins and glycolipids can be used as markers.

The first five of the markers listed above train the neural network in the preferred embodiment of the present invention. These five markers are used, not necessarily because they are the best markers on the list, but because these are markers for which the most patient data is available.

In reviewing marker data and preparing this data for input into the neural network, it is necessary to classify each marker as continuous or binary. The input data is encoded to indicate this aspect of the input marker. Further, it is helpful to remove false or misleading marker data which apparently provide a false data to the network. The range of data variation is limited so that extreme data is rejected. To do this, a software program scatterplot available in a spreadsheet such as Quatro Pro™ or Lotus 123™ eliminates outlier data which is 3.5 standard deviations from the mean for each given marker. Therefore, any data greater than 3.5 standard deviations is typically a faulty reading or recording error. If it is an actual reading, the patient likely has either an advanced cancer prognosis, or some other medical condition.

Each input marker must be encoded for entry into the neural network. The encoding scheme depends on the marker itself. Examples of possible encoding, not by way of limitation, include ratio, normalization, log transformation and first derivative (rate of change). The latter encoding scheme is frequently used for time series data. A single continuous or variable marker (over some range) may be encoded in a number of ways. Binary mode markers are encoded simply by their presence or absence. A new input marker may be defined by using the relationship of two or more markers to each other. Depending on the encoding scheme for each marker, one skilled in the art can determine the number of processing elements required to input all of the markers. In the present instance, each input marker is encoded as a single continuous variable, i.e., a measured variable over a range.

The number of output processing elements in the output layer depends on the information to be obtained from the output. If it is desired to diagnose whether or not the patient has colorectal cancer with an added validity or quality measure, two output processing elements are necessary; one indicating the presence or lack of cancer, and one indicating confidence or quality of the binary data. If there is limited input training, the confidence measure (i.e., zero to 100%) may be somewhat crude or coarse. As the training increases, when additional data becomes available, it may be possible to evaluate probability that the patient has colorectal cancer or also provide the degree of development of the disease, and provide more than two output data, hence, more than two processing elements. As an aside, when training a neural network, it is useful to have an extra processing element in the output to represent some mutually exclusive condition, as a means of providing a validity indication.

Once the input layer and output layer of the neural network are defined, it is necessary to define the hidden layers connected between input and output. Each input processing element is connected to each processing element in first hidden layer. Each processing element in the first hidden layer is connected to each processing element of the next sequential hidden layer. Processing elements within a hidden layer are not interconnected. Each processing element of the last hidden layer is connected to each output processing element. As hidden layer processing elements are increased, more complex patterns are learned.

Training of the neural network is accomplished by an iterative process. Each input processing element in the input layer inputs one marker, and each output processing element in the output layer represents a diagnostic variable such as whether the patient has colorectal cancer, i.e., one output is binary (whether or not cancer is present) and a second output indicates quality of the diagnosis. A third output indicates the inverse binary value to check data for logical consistency. Each of the connections between processing elements had a weight associated with it. The connection between one input marker element and one hidden layer processing element has a weight associated with it. During training of the network, the network outputs are compared with their corresponding target values (independent analytical data showing whether the patient did or did not have colorectal cancer). The error between the output and the target values is fed back through the network to update the weights (that is, to increment or decrement the weight of the connections) using the back propagation algorithm previously discussed.

The training goal is a network with sufficient hidden layer processing elements to capture the patterns of interaction involving the input data without providing so many hidden layer elements that the network merely memorizes the training data set and loses the capacity to generalize.

In the preferred embodiment of the present invention, the input layer is initially about 5 processing elements, the output layer is initially 2 output processing elements, and about 2 to about 15 hidden layers are connected between; further, the number of processing elements in each hidden layer ranges between about 10 to about 40. Preferably, the number of hidden layers ranges from about 2 to 10, with the total number of processing elements ranging from about 24 to about 100. In the case where the number of output layer processing elements is greater than 2, the total number of hidden layer processing elements may be increased without the network losing the capacity to generalize.

A variety of transfer functions operate on the information in the processing elements; a non-linear transfer function is preferable. A sigmoid transfer function (logit function) is acceptable.

During neural network training, typically, the neural network is provided with a chosen learning rate and a training tolerance. A learning rate that is too high will result in a failure to learn. The learning rate is adjusted as training progresses, to obtain the best results. The training tolerance is selected on the basis of the amount of variation permitted between the output of the network and the target value. Training of the network is successful when the output of the network correctly predicts the known disease status for a new (i.e., not seen before) set of patient input markers. Testing of the network is then carried out for one or more sets of data. If training is not successful, it is necessary to reconsider the network design. For example, one can alter the number of processing elements in the network, delete an input marker and add one having an improved relationship to colorectal cancer, add an additional marker, change the manner in which particular input marker data is encoded, or alter other features described above. Recall encoding is a ratio, a logrithmic value, etc.

As a final step in determining if the network is properly trained, the network must be tested. A testing tolerance is specified, so that the variation permitted between the output of the network and the target value is specified. Testing is best done using input marker data which the network has not previously seen. The diagnosis from the network output layer is compared with the actual status of the patient as determined by independent means. In other words, testing uses the data of a patient whose cancer status is known. Such training data can be collected over years for many hundreds of patients and is still useful as long as the disease mechanism remains unaltered. Collected data from hundreds of patients typically seen at a teaching hospital can be readily used.

Typical Neural Network

The FIGURE illustrates a typical neural network 100 which comprises layers and processing elements which fall within the range of layers and processing elements previously defined. More specifically, an input layer 110 comprises five processing elements 111, 112, 113, 114 and 115. Input data, such as biological markers and supplemental data such as patient age, sex, etc., are denoted by the arrows 50, 52, 54, 56 and 58 and are input into the processing elements 111–115 of the input layer 110. The FIGURE illustrates two hidden layers 120 and 130, and an output layer 140. The hidden layer 120 comprises fifteen processing elements, with only elements 201, 202 and 215 being shown or purposes oF clarity. The layer 130 comprises fifteen processing elements, with only elements 301, 302 and 315 being shown for purposes of clarity. The output layer 140 comprises two processing elements 142 and 142. The processing elements 401 and 402 yield the output data, such as the patient does have colorectal cancer or the patient does not have colorectal cancer, as illustrated conceptually by the arrows 60 and 62.

Representative interconnections between the processing elements are shown by lines. Stated another way, each interconnecting line represents the transfer or output from one processing element to another processing element for additional processing. As an example, line 80 represents a connection between the processing element 111 and the processing element 201 including an associated weighting factor. Line 82 represents a connection between the processing element 111 and 202 including an associated weighting factor. As discussed previously, every processing element in a given layer is connected to all processing elements in adjacent layers, but no connections exist between processing elements within a given layer.

It should be understood that the neural network 100 illustrated in the FIGURE is representative. The number of hidden layers can be varied, and the number of processing elements in the input layer, output layer, and hidden layers can also be varied within ranges previously defined.

EXAMPLE

The neural network software trained to diagnose colorectal cancer was a Brainmaker Professional V 2.51 available from California Scientific Software of Nevada City, Calif. The data used in these analyses were obtained from the University of Texas M. D. Anderson Cancer Research Center and the Kelsey-Seybold Clinic, P. A. at Houston, Tex.

Individual patients in the following groups provided serial blood tested for serum markers namely, Group 1 comprised of 57 Normal non-acute GI Donors and Group 2 was 12 patients known to have colorectal cancer (before any treatment). Group 3 includes patients with colorectal polyps (at high risk for cancer). This latter group of patients exhibited higher than normal variation in tumor markers presence, although some of the variation in the markers might have indicated the development of another kind of cancer other than colorectal cancer.

Blood samples were collected from the participating patients at the following timed examinations over three years. For Group 1, the tests were done initially and at 1, 3, 6, 9, 12 and 24 months, depending on patient availability. For Group 2, tests were done initially and at 1, 3, 6, 9, 12, 24, 30 and 36 months; and for Group 3, test were done initially and at 1, 3, 6, 9, 12, 24, 30 and 36 months. The many patients have common data taken at times of zero (the starting data) and also 1, 3, 6, 9, 12, and 24 months.

Marker test results from the initial samples were input to the neural network in the preferred embodiment of the present invention. Group 1 individuals defined normal variation of the makers. Marker test results from Group 2 individuals provided marker input associated with the definite presence of fully developed colorectal cancer. Marker test results from Group 3 individuals provide marker input to the neural network for individuals having a high probability of developing colorectal cancer.

Five biological indicators, or markers were measured using known analytical techniques and the serum samples taken from the patients described above. The five markers measured were:

Carcinoembryonic Antigen (CEA), as measures using an Immunoassy Test Kit available from Roche Diagnostic Systems, Division of Hoffmann-LaRoche Incl, Nutley, N.J. The measured data are micrograms per liter.

Alpha-Fetoprotein Modified for Increased Analytical Precision (AFP), as determined using the method described by Shahram Shahangian et al. in Clinical Chemistry, Vol. 33, No. 4, 1987, pp. 583–586. The measured data are in micrograms per liter.

Antigen specific for #1116-N5'-19-9 antibody as determined using the procedure specified by Centocor in its Carbohydrate Aatigen 19-9™ Radioimmunoassay test kit, available from Centocor of Malvern, Pa. The data generated are specific to this test and are defined in units per milliliter.

Pancreatic Oncofetal Antigen (POA) as determined using the method described by Sharam Shahangian et al. in Clinical Chemistry, Vol. 35, No. 3, 1985, pp. 405–408. The units measured are in milligrams per liter.

Improved Method to Determine Lipid Bound Sialic Acid in Plasma or Serum (LSA) as determined using the method described by Nonda Katopodis et al. in Research Communications in Chemical Pathology and Pharmacology, Vol. 30, No. 1, Oct. 1980, pp. 171–180. The units measured are in milligrams per liter.

Table 1 lists the data for the Group 1 Patients input to the Brainmaker Special V2.51 neural network program. The data for 57 normal patients was input into the neural network.

TABLE 1

| Patient No. | LSA | AFP | POA | CEA | Antigen '19-9 |
| --- | --- | --- | --- | --- | --- |
| 1 | 213 | 3.7 | 5.1 | 0.2 | 7.5 |
| 2 | 151 | 1.8 | 8.1 | 0.0 | 27.4 |
| 3 | 199 | 8.4 | 7.1 | 0.0 | 0.0 |
| 4 | 160 | 5.8 | 12.9 | 0.3 | 7.9 |
| 5 | 145 | 5.2 | 4.8 | 0.0 | 0.0 |
| 6 | 123 | 3.4 | 6.8 | 0.0 | 12.8 |
| 7 | 151 | 4.9 | 6.2 | 0.0 | 20.1 |
| 8 | 161 | 1.7 | 10.4 | 0.0 | 20.3 |
| 9 | 146 | 3.5 | 5.2 | 0.4 | 2.8 |
| 10 | 163 | 4.0 | 7.3 | 0.0 | 14.6 |
| 11 | 225 | 5.2 | 4.4 | 2.6 | 20.7 |
| 12 | 169 | 3.0 | 3.4 | 0.0 | 1.8 |
| 13 | 191 | 2.7 | 8.7 | 0.0 | 25.7 |
| 14 | 137 | 1.1 | 15.7 | 0.5 | 1.1 |

TABLE 1-continued

| Patient No. | LSA | AFP | POA | CEA | Antigen '19-9 |
| --- | --- | --- | --- | --- | --- |
| 15 | 261 | 0.2 | 12.4 | 0.0 | 0.0 |
| 16 | 123 | 2.1 | 6.9 | 0.0 | 13.9 |
| 17 | 140 | 1.8 | 7.0 | 0.0 | 0.0 |
| 18 | 181 | 2.8 | 5.4 | 0.0 | 1.0 |
| 19 | 164 | 6.4 | 7.5 | 0.8 | 23.2 |
| 20 | 166 | 1.1 | 3.9 | 0.3 | 1.2 |
| 21 | 202 | 0.5 | 8.6 | 0.0 | 2.9 |
| 22 | 169 | 4.5 | 7.0 | 0.0 | 7.4 |
| 23 | 142 | 1.5 | 8.4 | 0.0 | 2.5 |
| 24 | 127 | 5.3 | 9.7 | 0.7 | 15.5 |
| 25 | 203 | 2.0 | 6.8 | 0.7 | 8.9 |
| 26 | 169 | 4.2 | 4.7 | 0.0 | 8.9 |
| 27 | 147 | 6.7 | 5.3 | 0.0 | 5.1 |
| 28 | 185 | 5.2 | 7.3 | 0.0 | 2.2 |
| 29 | 154 | 5.2 | 4.9 | 2.5 | 29.8 |
| 30 | 133 | 5.0 | 5.4 | 0.0 | 0.0 |
| 31 | 123 | 0.7 | 6.0 | 0.0 | 37.1 |
| 32 | 177 | 2.2 | 22.9 | 2.3 | 8.4 |
| 33 | 179 | 6.5 | 6.7 | 3.7 | 10.2 |
| 34 | 130 | 1.5 | 5.9 | 0.0 | 21.6 |
| 35 | 184 | 1.7 | 11.0 | 0.4 | 7.2 |
| 36 | 180 | 2.6 | 6.7 | 2.6 | 7.3 |
| 37 | 184 | 4.6 | 15.2 | 0.0 | 0.0 |
| 38 | 119 | 3.2 | 10.6 | 1.0 | 2.9 |
| 39 | 182 | 3.2 | 5.9 | 0.0 | 4.7 |
| 40 | 173 | 3.7 | 6.5 | 0.0 | 2.7 |
| 41 | 187 | 0.6 | 7.2 | 0.0 | 18.0 |
| 42 | 181 | 4.6 | 5.2 | 0.5 | 3.2 |
| 43 | 153 | 3.4 | 10.7 | 0.0 | 10.2 |
| 44 | 194 | 2.9 | 5.9 | 0.0 | 0.0 |
| 45 | 186 | 1.6 | 9.4 | 0.6 | 10.4 |
| 46 | 131 | 3.8 | 4.8 | 0.0 | 2.5 |
| 47 | 211 | 5.5 | 7.8 | 0.7 | 0.0 |
| 48 | 198 | 1.9 | 4.8 | 0.0 | 13.8 |
| 49 | 145 | 4.1 | 2.5 | 0.1 | 7.4 |
| 50 | 154 | 8.7 | 6.1 | 0.0 | 47.4 |
| 51 | 213 | 7.1 | 9.1 | 6.2 | 14.1 |
| 52 | 147 | 5.8 | 5.6 | 0.0 | 6.3 |
| 53 | 125 | 0.9 | 5.8 | 0.0 | 29.4 |
| 54 | 172 | 0.7 | 8.1 | 0.0 | 2.1 |
| 55 | 140 | 4.1 | 6.9 | 0.6 | 2.0 |
| 56 | 106 | 6.4 | 4.8 | 0.3 | 25.5 |
| 57 | 165 | 1.6 | 5.8 | 0.0 | 10.7 |

Table 2 below lists the date for the Group 2 Patients input to the Brainmaker Special V2.51 neural network program. Data was collected for 12 patients and was input into the neural network.

TABLE 2

| Patient No. | LSA | AFP | POA | CEA | Antigen '19-9 |
| --- | --- | --- | --- | --- | --- |
| 1 | 198 | 3.6 | 7.0 | 0.0 | 64.1 |
| 2 | 234 | 2.6 | 7.1 | 0.0 | 3.9 |
| 3 | 195 | 4.3 | 16.8 | 0.0 | 16.3 |
| 4 | 330 | 2.7 | 11.1 | 0.0 | 8.7 |
| 5 | 196 | 8.0 | 9.1 | 0.9 | 10.1 |
| 6 | 170 | 0.8 | 5.5 | 0.0 | 3.8 |
| 7 | 213 | 6.1 | 4.8 | 1.1 | 0.9 |
| 8 | 213 | 7.0 | 11.2 | 8.3 | 15.8 |
| 9 | 197 | 0.9 | 7.0 | 0.0 | 0.7 |
| 10 | 218 | 2.2 | 7.2 | 0.0 | 8.2 |
| 11 | 385 | 2.5 | 1O.5 | 0.2 | 11.5 |
| 12 | 184 | 1.3 | 9.1 | 0.0 | 0.0 |

The parameters which were entered into the neural network software to set limitations on operation of the system were as follows:

| Training Tolerance Tuning: | Learning Rate Tuning: | |
|---|---|---|
| | Correct | Rate Multiplier |
| Initial Tolerance: 0.100 | 0% | 1.000 |
| Ending Tolerance: 0.100 | 50% | 1.000 |
| Multiply Tolerance By: 0.800 | 75% | 1.000 |
| At: 100% Correct | 90% | 1.000 |
| Testing Tolerance: 0.400 | | |

Aadd neuron to each hidden layer if rms error does not ratably decrease over N runs (where N is a whole number).

| | Layer | Learn Rate | Smoothing |
|---|---|---|---|
| Maximum Training Runs: 999999 | 1 | 1.000 | 0.900 |
| Test Every N Training Runs: 0 | 2 | 1.000 | 0.900 |
| Train At End Of Run Only: N | 3 | 1.000 | 0.900 |

Initial Network Size

| Layer | Processing Elements or Neurons | Connections (Including Bias Element) |
|---|---|---|
| Input | 5 | — |
| 1 | 15 | 90 |
| 2 | 15 | 240 |
| 3 | 2 | 32 |

Four independent networks were trained using the data from Tables 1 and 2. The training data for a single network contained 90% of the total data in Tables 1 and 2. Training data was randomly selected from Tables 1 and 2. Each training data set included at least one patient from Table 2. The remaining 10% of the data from Tables 1 and 2 was used to test this network. This procedure was followed for each of the independent networks.

Testing of the networks indicated that a trained network can diagnose the presence of colorectal cancer in an individual patient with a sensitivity of 60% and a specificity of 86%.

In the foregoing tests the measurements from the 57 patients making up Group 1 and 12 patients making up Group 2 can be used to train the system for diagnosis of patients having data never seen before. Patients from Group 3 are evaluated to determine relative probability of developing cancer or at least having precancerous conditions.

The minimal output described for the system is a simple binary indication that the patient does or does not have cancer, and a second data which is indicative of the confidence or quality of that binary indication. While the binary condition is represented simply as a two state answer (either the patient does or does not have cancer), the quality of that conclusion is indicated in a numeric range, and representative quality assessments can be on some numeric scale. As an easy example, the quality diagnosis can be represented between zero and 100%.

One precancerous condition is the presence or absence of polyps located in the colon. The present system is not specific to locating polyps as a precancerous condition but rather is a broader approach evaluating all aspects of the precancerous state. The developmental status may manifest a number of polyps in some patients while others may not have any polyps. While polyps have heretofore been a typical examined aspect of precancerous development, the analytical system of this disclosure is able to provide a more expansive indication of the precancerous development in the patient. In that sense, it provides better early warnings and is not tied categorically to polyp developments.

Additional outputs of the present invention are outputting of data indicating both the severity of precancerous development and the quality or confidence level of that. This can have the form of third and fourth output elements from the neural network. The precancerous status of the patient can be defined in some typified numeric scale, i.e., ranging from zero to 10 where 10 indicates the occurrence of cancer and the gradations to 9 represent lesser states and zero defines the patient who is completely devoid of symptoms. Again, a quality factor represented by a number of zero to 100% is included.

Going back to the data in the tables, it will be recalled that the data is collected for a particular set of patients at specific intervals. The rate of change of the five variables making up the reported tables above can be also included to add five rate values. Alternately, the table data can be doubled or tripled by inputting the data at specific timed intervals. As an example, the data of the patients in Groups 1 and 2 is input for the initial examination, and for a later examination date occurring at some interval, i.e., after 3 months, after 6 months or one year. In effect, this inputs three sets of data, two of them being the absolute measurements just noted at specific times intervals, and the third representing the time based rate change in the measurements. This time based trend measurement is significant in evaluation.

In another aspect of the present disclosure, a weighting factor a sixth column in the tables) represents the family history. Here again, that can be defined as a set of weights which range from zero to some arbitrary maximum value such as ten. If there is simply no colon cancer in the history of the family, the weight can be set at zero while it is set at the maximum value if both parents of the patient had colon cancer. Intermediate values are indicative of cancer occurrence in siblings, grandparents, and other family members. Additional input data includes other medical history or demographic material. The precise choice of such patient demographic material from a personalized medical history can vary depending on definitions assigned to the input data markers. An example was given above with regard to family history. Examples of a useful sort involve age, weight, race, sex, and other objective indicia obtained in a medical history.

The neural network is configured to direct medical treatment short of the highly invasive procedures otherwise required. While invasive procedures may be required. they arc more precisely directed after diagnosis through the present invention. Prior to any invasive procedure, the present invention readily screens the patient so that invasive procedures are deferred; they can be reserved for those patients where the indications strongly urge further diagnosis.

The above-described preferred embodiments of the present invention are not intended to limit the scope of the present invention as demonstrated by the claims which follow, as one skilled in the art can, with minimal experimentation, expand the principals of the invention to the claimed scope of the invention. While the foregoing is directed to the preferred embodiment, the structure is determined by the claims which follow.

We claim:

1. A method of preparing for and then diagnosing colon cancer risk, the method comprising the steps of:

(a) selecting data markers having a sufficient relationship with the development of or presence of colorectal cancer, wherein the selected input data markers indicate patient;
  (i) likelihood of developing colon cancer,
  (ii) has a high probability of colon cancer, or
  (iii) has colon cancer; or
(b) obtaining a set of patient bodily fluids including markers therewith
(c) developing an encoding scheme for each of said input data markers; and
(d) evaluating the encoded input data markers for cancer risk.

2. The method of claim 1 wherein the step of evaluating comprises the steps of:
  (e) determining a total number of input processing elements needed in relationship to the number of input data markers and the encoding scheme used for each of said input data markers;
  (f) using output elements including at least one output element representing mutually exclusive conditions;
  (g) determining the number of individual processing elements connected between said input and output processing elements wherein the individual processing elements are arranged in a set of processing layers;
  (h) selecting a transfer function for said processing elements;
  (i) selecting a learning rate and training tolerance; and
  (j) inputting data markers to said input processing elements to obtain an output element diagnosis.

3. The method of claim 2 wherein iterative evaluations are done through a neural network characterized by:
  (a) an input layer having at least two marker inputs;
  (b) at least one hidden layer wherein each hidden layer has at least five processing elements;
  (c) an output layer having at least one output; and
  wherein marker data are processed iteratively so that known patient marker data provides an output consistent with the cancer condition of the known patients.

4. The method of claim 2 wherein the step of obtaining output element diagnosis is done by a connectionist, non-linear analytical iterative process through a neural network having the following characteristics:
  (a) an input layer having at least N marker input where N equals the number of markers;
  (b) at least one hidden layer, wherein every hidden layer has at least five processing elements; and
  (c) an output layer having at least one output indicating colon cancer probability.

5. The method of claim 1 wherein said selected data markers include at least two markers selected from the group consisting of Carcinoembryonic Antigen (CEA); Alpha-Fetoprotein Modified for Increased Analytical Precision (AFP); Pancreatic Oncofetal Antigen (POA); Antigen Specific for #1116-N5'-19-9 Antibody; Lipid-Bound Sialic Acid (LSA); New oncogenes; Myc oncogenes; Ras oncogenes; Centocor CQA 72/4 (a measurement of tumor-associated Glycoprotein 72 (TAG-72) using epitope-specific antibody # B72-3); Antibodies for the p53 gene; Antibodies to Laminin $-P_1$; Yale Col. Sr. Factor; Harvard Urinary gonadotropin Peptide (UGP); Tumor Suppressor Gene p53; and antibodies to the markers listed in cases where the marker is not an antibody.

6. The method of claim 1 wherein said selected data markers include at least two markers selected from the group consisting of Carcinoembryonic Antigen (CEA); Alpha-Fetoprotein Modified for Increased Analytical Precision (AFP); Pancreatic Oncofetal Antigen (POA); Antigen Specific for #1116-N5'-19-9 Antibody; Lipid-Bound Sialic Acid (LSA); and antibodies to said markers in cases wherein said marker is not an antibody.

7. The method of claim 6 wherein said neural network is initially trained so that said network additionally provides a binary indication that the patient does or does not have colon cancer.

8. The method of claim 7 including the steps of
  (a) inputting patient demographic data to the neural network;
  (b) inputting marker data by indicating the presence or absence of such markers and the amount of markers present.

9. The method of claim 7 wherein said patient body fluids are collected repetitively from a patient over a period of time to obtain at least two sets of timed markers.

10. A diagnostic screening or risk assessment is produced using the method of claim 7.

11. The method of claim 10 wherein the step of evaluating is performed with a neural network.

12. The method of claim 1 including the ssteps of initially training neutral network with marker data of patients known to have colon cancer and of patients known not to have colon cancer.

13. A method of diagnosing cancer of the colon to determine whether a patient has a probability of developing cancer of the colon wherein the method comprises the steps of:
  (a) sampling from a patient a set of body fluids;
  (b) extracting from the body fluids a set of colon cancer markers having a sufficient relationship with the development of or the presence of colon cancer to enable patient diagnosis;
  (c) measuring the body fluid markers to obtain marker data; and
  (d) evaluating the marker data to determine from the markers patient diagnosis of colon cancer, wherein the step of evaluating the marker data includes
    (i) indicating whether the patient has colon cancer, or
    (ii) indicating whether the patient has a high probability of colon cancer, or
    (iii) indicating the likelihood of the patient developing colon cancer.

14. The method of claim 13 wherein the step of evaluating the marker data includes the step of correlating marker concentration to historical marker concentration.

15. The method of claim 13 wherein the step of evaluating the marker data iteratively correlates the marker data to obtain a binary indication whether the patient has colon cancer; and the evaluation also includes correlating marker concentration with historical marker concentration data of patients known to have colon cancer.

16. The method of claim 15 including the evaluation step of iteratively correlating the marker data through a neural network.

17. The method of claim 16 wherein the iteratively evaluations are done through a neural network characterized as:
  (a) an input layer having at least two marker inputs;
  (b) at least one hidden layer wherein each hidden layer has at least five processing elements;
  (c) an output layer having at least one output; and
  wherein marker data are processed iteratively so that known patient marker data provides an output consistent with the cancer condition of the known patients.

18. A method of diagnosing cancer of the colon to determine probability of colon cancer development comprising the steps of:
(a) obtaining from a patient a set of samples of body fluids;
(b) extracting from the body fluids a set of colon cancer markers having a sufficient relationship with the development of colon cancer to enable patient diagnosis;
(c) measuring the body fluid markers to obtain patient marker data;
(d) evaluating the patient marker data to provide patient colon cancer probability wherein the step of evaluating includes inputting the patient marker data to a non-linear relationship and determining from the relationship a measure of probability of colon cancer, wherein the step of evaluating is a connectionist, non-linear analytical iterative process comprising
 (i) an input layer having at least N marker input where N equals the number of markers,
 (ii) at least one hidden layer, wherein each hidden layer has at least five processing elements, and
 (iii) an output layer having at least one output indicating colon cancer probability.

19. The method of claim 18 wherein the number N of said marker inputs ranges from four to about ten, and the number of hidden layers ranges from two to about fifteen.

20. The method of claim 19 wherein the number of hidden layers ranges from two to about ten and wherein the total number of processing elements ranges from about twenty-four to about one hundred.

* * * * *